(12) United States Patent
Rust et al.

(10) Patent No.: US 6,900,332 B2
(45) Date of Patent: May 31, 2005

(54) PROCESS FOR THE PREPARATION OF SUBSTITUTED OXAZOLES

(75) Inventors: Harald Rust, Neustadt (DE); Kirsten Burkart, Ludwigshafen (DE); Tillmann Faust, Weisenheim (DE); Jochem Henkelmann, Mannheim (DE); Alois Kindler, Grüstadt (DE); Christian Knoll, Neuhofen (DE); Michael Becker, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/348,961

(22) Filed: Jan. 23, 2003

(65) Prior Publication Data

US 2003/0125567 A1 Jul. 3, 2003

Related U.S. Application Data

(63) Continuation-in-part of application No. 10/209,529, filed on Aug. 1, 2002, now abandoned.

(30) Foreign Application Priority Data

Aug. 3, 2001 (DE) .......................................... 101 37 480
Mar. 5, 2002 (DE) .......................................... 102 09 446

(51) Int. Cl.[7] ............................................ C07D 263/30
(52) U.S. Cl. ........................................ 548/228; 546/50
(58) Field of Search ........................... 548/228; 546/250

(56) References Cited

FOREIGN PATENT DOCUMENTS

| DE | 30 29 231 | 3/1982 |
|---|---|---|
| JP | 54020493 | 1/1979 |
| SU | 68 1057 | 8/1997 |

OTHER PUBLICATIONS

Chem.Rev.,1975,vol. 75, No. 4, Turchi et al.
Ullmann's Enc.,Ind.Chem.1996,vol. A27, 533–537.
Greene,Protective Groups in Org.Syn.1981, 14–71.
Kocienski,Protecting Groups, 1994, 21–94.
Itov.et al.,Solvent Effect on the Termal Cyclization of . . . 1632–1636 , 1978.
Methods of Synthesis and Tech.of Drug Prod.,568–572, Mishchenko et al. 1988.
Bull.Chem.Soc.Japan, vol. 44, 1407–1410, Maeda et al.
Chem.Ber. 1961, 94, 2814, Ugi et al.
Chem.Ber.1960,93,239–248, Ugi et al.
Agnew.Chem. 1965, 77, 492–504 Ugi et al.
Chem. Ber. 108,1975,1580–1590.
Derwent J79020–493.

*Primary Examiner*—Kamal Saeed
(74) *Attorney, Agent, or Firm*—Novak Druce & Quigg, LLP

(57) ABSTRACT

The present invention relates to a process for preparing 5-alkoxy-substituted oxazoles, in particular for preparing 4-methyl-5-alkoxy-substituted oxazoles and also a process for preparing pyridoxine derivatives.

22 Claims, 1 Drawing Sheet

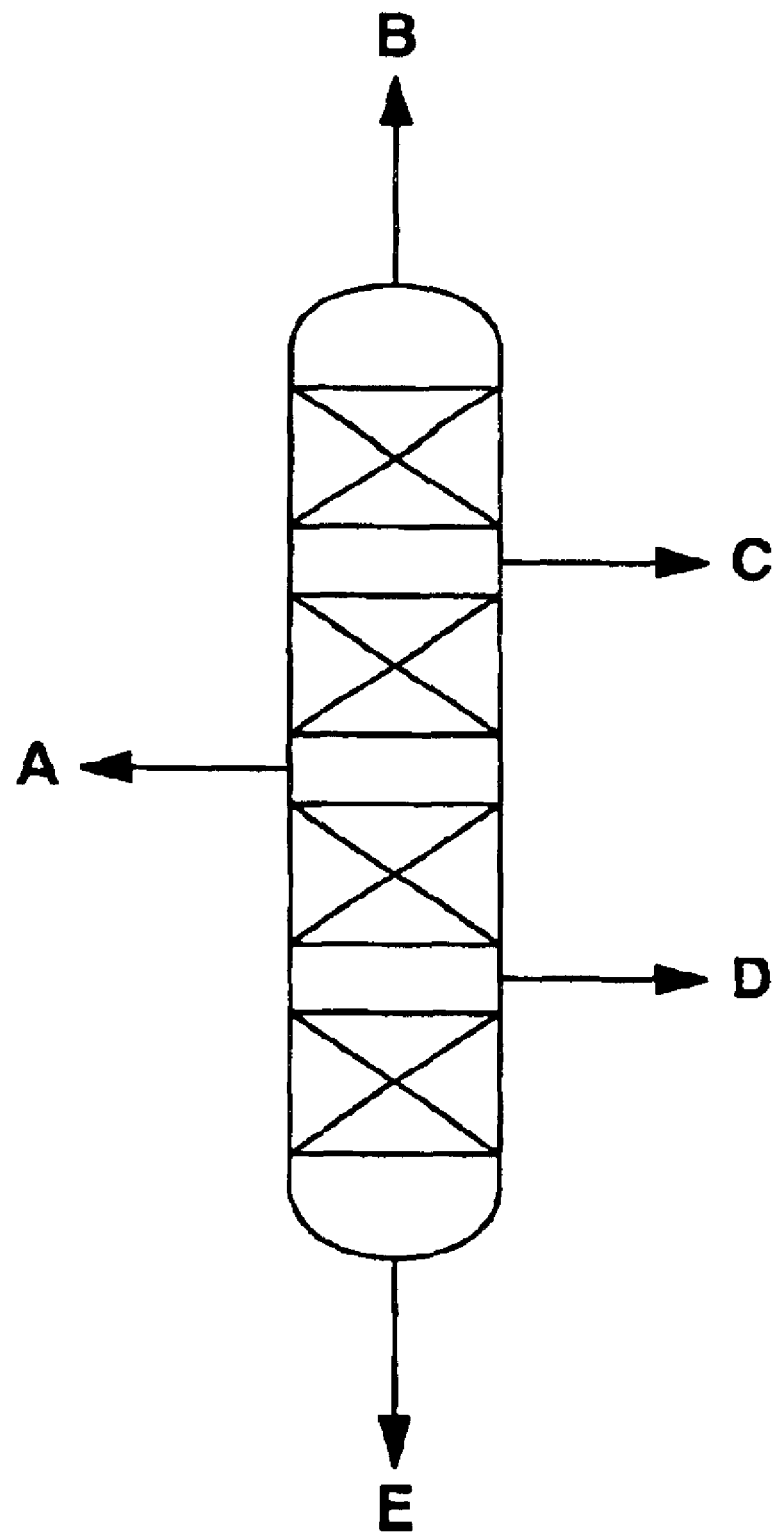

PROCESS FOR THE PREPARATION OF SUBSTITUTED OXAZOLES

This is a Continuation in Part application of application Ser. No. 10/209,529, filed on Aug. 1, 2002, now abandoned.

The present invention relates to a process for preparing 5-alkoxy-substituted oxazoles, in particular for preparing 4-methyl-5-alkoxy-substituted oxazoles and also a process for preparing pyridoxine derivatives.

5-alkoxy-substituted oxazoles are valuable building blocks in organic chemistry. 4-methyl-5-alkoxy-substituted oxazoles have particular significance as important precursors for the synthesis and industrial production of vitamin $B_6$ (Turchi et al., Chem. Rev. 1975, 75, 416).

A process which is economically viable and is operable on a large scale for preparing 5-alkoxy-substituted oxazoles, in particular 4-methyl-5-alkoxy-substituted oxazoles, is therefore of great significance.

It is known that α-isocyanoalkanoate esters can be converted batchwise by thermal isomerization into the corresponding 5-alkoxy-substituted oxazoles.

Itov et al., Khimiko-Farmatsevticheskii Zhurnal, 1978, 12, 102–106 and Mishchenlo et al., Khimiko-Farmatsevticheskii Zhurnal, 1988, 7, 856 to 860 describe a batchwise thermal cyclization of α-isocyanopropionate esters to give the corresponding 4-methyl-5-alkoxy-substituted oxazoles at 135° C. The yields of 4-methyl-5-alkoxy-substituted oxazoles achieved by the use of various solvents are from 4 to 36%. The process has the disadvantage of low selectivity and thus the disadvantage that large amounts of by-products are formed. The most frequent by-products of this reaction are the unconverted reactant (Yield: 33 to 55%) and also the rearranged α-nitrilopropionate ester (yield 1 to 39%).

Maeda et al., Bull. Chem. Soc. Japan, 1971, 44, 1407 to 1410 disclose a batchwise thermal cyclization of various α-isocyanocarboxylate esters to give the corresponding 5-alkoxy-substituted oxazoles at temperatures of from 150 to 180° C. Depending on the substituents, yields from 5.1 to 28.2% are achieved.

JP 54-20493 describes a batchwise process for preparing 4-methyl-5-alkoxy-substituted oxazoles by thermally cyclizing α-isocyanopropionate esters at temperatures of 155 to 170° C. in the presence of a tertiary amine. After the end of the reaction, the solution is fractionally distilled under reduced pressure at very low temperatures. Although improved selectivities for the desired oxazoles are achieved (from 34 to 91.5%), the low conversion (from 11.1 to 49.4%) leads to yields which are still unsatisfactory.

All of the prior art processes have the disadvantage of low conversions and low selectivities and thus low yields of 5-alkoxy-substituted oxazoles.

It is an object of the of the present invention to provide a further process for preparing 5-alkoxy-substituted oxazoles which has advantageous characteristics, does not have the disadvantages of the prior art and delivers the 5-alkoxy-substituted oxazoles at high conversions in high selectivities and yields.

We have found that this object is achieved by a process for preparing 5-alkoxy-substituted oxazoles of the formula I,

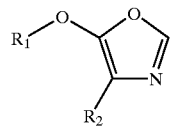

where
$R_1$ is an unsubstituted or substituted $C_1$–$C_6$-alkyl radical and
$R_2$ is hydrogen or an unsubstituted or substituted $C_1$–$C_6$-alkyl radical,
which comprises
converting α-isocyanoalkanoate esters of the formula II

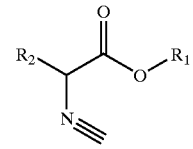

in the presence of assistants
at temperatures above 80° C.
to the 5-alkoxy-substituted oxazoles of the formula I
and, simultaneously with the conversion, removing the 5-alkoxy-substituted oxazoles of the formula I from the reaction mixture.

The $C_1$–$C_6$-alkyl radicals $R_1$ and $R_2$ are each independently branched or unbranched, substituted or unsubstituted $C_1$–$C_6$-alkyl radicals, for example, substituted or unsubstituted methyl, ethyl, propyl, 1-methylethyl, n-butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, hexyl, 1-methylpentyl, 1,2-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl or 2-ethylbutyl.

The nature of the substituents is not critical. The $C_1$–$C_6$-alkyl radicals may, depending on the possibility of free bonds, contain up to 6 substituents, preferably selected from the group consisting of aryl, hydroxyaryl, —$NO_2$, —$NH_2$, —OH, —CN, —COOH, or halogen, in particular F or Cl.

In a preferred embodiment, the $C_1$–$C_6$-alkyl radicals of the radicals $R_1$ and $R_2$ are unsubstituted.

Preferred $R_1$ radicals include $C_1$–$C_4$-alkyl radicals, for example, methyl, ethyl, isopropyl, n-propyl, n-butyl, sec-butyl or tert-butyl, more preferably n-butyl.

Preferred $R_2$ radicals include hydrogen and $C_1$–$C_4$-alkyl radicals, for example, methyl, ethyl, iso-propyl, n-propyl, n-butyl, sec-butyl or tert-butyl, more preferably methyl.

Preference is given to the combination of the preferred radicals for $R_1$ and $R_2$, and particular preference to the combination of $R_1$=n-butyl and $R_2$=methyl.

In a particularly preferred embodiment of the process according to the invention, n-butyl α-isocyanopropionate is accordingly converted into 4-methyl-5-n-butoxyoxazole.

The α-isocyanoalkanoate esters of the formula II used in the process according to the invention may be of any desired purity.

The α-isocyanoalkanoate esters of the formula II are prepared in a manner known per se from the corresponding formamido acid esters of the formula V

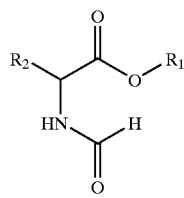

by reacting them with phosphorus oxychloride or phosgene in the presence of bases. Common synthetic methods are described in Itov et al., Khimiko-Farmatsevticheskii Zhurnal, 1978, 12, 102–106; Maeda et al., Bull. Chem. Soc. Japan, 1971, 44, 1407–1410; Ugi et al., Chem. Ber. 1961, 94, 2814; Chem. Ber. 1960, 93, 239–248, Angew. Chem. 1965, 77, 492–504, Chem. Ber. 1975, 1580–1590, DE 30 29 231 A1 and J. Heterocyclic Chemistry 1988, 17, 705.

For the purposes of the present invention, assistants are chemical compounds, preferably chemical compounds which accelerate cyclization reaction or shift the thermodynamic equilibrium in the direction of the desired product. Preferred assistants include cyclizing assistants selected from the group consisting of bases, alcohols and esters.

For the purposes of the present invention, bases are compounds having Brønsted base properties. Preferred bases include tertiary amines, for example, triethylamine, triisopropylamine, tri-n-butylamine, di-methylcyclohexylamine, tris(2-ethylhexyl)amine, N-methylpyrrolidone, N,N,N',N'-tetramethyl-1,3-propanediamine, N,N-diethylaniline or N,N-dibutylaniline. Particular preference is given to the use of tri-n-butylamine as base.

Preferred alcohols are substituted or unsubstituted $C_1$–$C_6$-alkanols, for example, methanol, ethanol, n-propanol, isopropanol, n-butanol, sec-butanol, tert-butanol, n-pentanol or n-hexanol. Particular preference is given to the use of n-butanol as alcohol.

Preferred esters include substituted or unsubstituted $C_1$–$C_6$-alkyl $C_1$–$C_6$-alkanoates, for example, methyl acetate, ethyl acetate, propyl acetate, n-butyl acetate, tert-butyl acetate, hexyl acetate, methyl propionate, ethyl propionate, propyl propionate, n-butyl propionate, tert-butyl propionate, hexyl propionate, methyl butanoate, ethyl butanoate, propyl butanoate, n-butyl butanoate, tert-butyl butanoate, or hexyl butanoate. Particular preference is given to the use of n-butyl propionate as an ester.

The assistants may be used as individual compounds or in the form of mixtures. Preference is given to using the assistants as individual compounds.

Below 80° C., no noticeable thermal cyclization takes place. The temperature of the conversion according to the invention is accordingly at least 80° C.

In a preferred embodiment, the process according to the invention is operated at temperatures of from 100 to 200° C., more preferably at temperatures from 120 to 170° C., most preferably at temperatures from 130 to 170° C.

The molar ratio of assistant to α-isocyanoalkanoate ester of the formula II is not critical and is preferably 10:1 to 0.05:1.

The process according to the invention can be carried out in particular, batchwise, semi-batchwise or continuously.

In a preferred embodiment of the process according to the invention, the process is carried out batchwise or semi-batchwise.

In a batchwise process, the α-isocyanoalkanoate esters of the formula II and the assistants are initially charged into a reactor and the α-isocyanoalkanoate esters are converted at temperatures above 80° C. to the 5-alkoxy-substituted oxazoles of the formula I, while, simultaneously with the conversion, removing the 5-alkoxy-substituted oxazoles of the formula I from the reaction mixture.

There are many reactor designs which are suitable for the preferred batchwise processing method. Preferred reactors should have the characteristic of facilitating a conversion while simultaneously removing a reaction product.

For example, useful reactors for the batchwise processing method include back-mixed reactors, for example, loop reactors, and customary batchwise reactors, for example tanks of all designs, equipped with an emplaced reaction column.

In a semi-batchwise process, the α-isocyanoalkanoate esters of the formula II and the assistants are are added semibatchwise to a reactor and the α-isocyanoalkanoate esters are converted at temperatures above 80° C. to the 5-alkoxy-substituted oxazoles of the formula I, while, simultaneously with the conversion, removing the 5-alkoxy-substituted oxazoles of the formula I from the reaction mixture.

There are many reactor designs which are suitable for the semi-batchwise processing method. Preferred reactors should have the characteristic of facilitating a conversion possible while simultaneously removing a reaction product.

For example, useful reactors for the semi-batchwise processing method include loop reactors, membrane reactors and customary semi-batchwise reactors, for example tanks of all designs, equipped with an emplaced reaction column.

In a preferred embodiment, the process is carried out in a batchwise or semi-batchwise reactor equipped with an emplaced reaction column and, simultaneously to the conversion, the 5-alkoxy-substituted oxazoles of the formula I are removed from the reaction mixture by rectification.

As is known to those skilled in the art, the term "column" in the following discussion refers, unless otherwise stated, to a column construction having a liquid phase. Accordingly, an "emplaced column" refers only to a column construction without a liquid phase.

Reaction columns and emplaced reaction columns preferably refer to columns whose internals have a hold-up, for example, columns having trays, beds, structured packings or random packings.

Particularly advantageous column trays facilitate a long residence time of the liquid, and the residence time on the internals of the reaction column is preferably at least 30 min.

Examples of preferred column trays include valve trays, preferably bubble-cap trays, or related designs, for example, tunnel cap trays, Lord stages and other internals and Thormann trays.

Examples of preferred structured packings include structured packings of the Mellapack® (Sulzer), BY® (Sulzer), B1® (Montz) or A3® (Montz) types or packings having comparable designs.

The reaction columns and emplaced reaction columns may be configured as desired by the construction and the internals. Particular preference is given to the use of a dividing wall column as the reaction column.

A reaction column or emplaced reaction column which can be configured in highly varied ways has the characteristic of being a reactor which can simultaneously facilitate a conversion of reactants and the removal by rectification of the 5-alkoxy-substituted oxazoles of the formula I from the reaction mixture.

In this preferred embodiment of the batchwise or semi-batchwise processing method while using a batchwise or semi-batchwise reactor equipped with an emplaced reaction column, it is also advantageous to set the rectification parameters in such a way that D the α-isocyanoalkanoate esters of the formula II are converted to the 5-alkoxy-substituted oxazoles of the formula I in the reactor and/or on the internals of the emplaced reaction column and E the 5-alkoxy-substituted oxazoles of the formula I resulting from the conversion are removed via the emplaced reaction column.

Depending on the design of the reactor, the emplaced reaction column and the reactants used, this is achieved by different settings of the rectification parameters. Examples of suitable rectification parameters include temperature, pressure, reflux ratio in the column, configuration of the column and its internals, heat transfer and energy introduction, each of which may be optimized through routine experiments by those skilled in the art in such a way that the features D and E are achieved.

In the batchwise and semi-batchwise processing methods, the pressure at the top of the column of the emplaced reaction column is set in such a way that the temperature in the reactor and on the internals is at least 80° C., preferably from 100 to 200° C., more preferably from 120 to 170° C., most preferably 130 to 170° C.

Typically, the top pressure of the column is set to from 5 to 800 mbar, in such a way that the bottom pressure resulting from the column type used and the tanks of any column internals used is typically from 5 mbar to atmospheric pressure.

It is possible that the 5-alkoxy-substituted oxazoles of the formula I form an azeotropic mixture with the assistants used so that the 5-alkoxy-substituted oxazoles of the formula I are removed via the emplaced column as an azeotropic mixture.

In this case, it is advantageous to set the top pressure and therefore also automatically the bottom pressure in the column in such a way that, depending on the 5-alkoxy-substituted oxazole of the formula I prepared and the assistants used, the fraction of assistant in the azeotrope in the top stream is as low as possible.

The assistants are removed from the azeotrope is in this case by a manner known per se, for example by a subsequent second rectification using a different pressure (two-pressure distillation).

For example, the 4-methyl-5-n-butoxyoxazole prepared by the process according to the invention forms an azeotrope with the base tri-n-butylamine. When a top pressure of 100 mbar is set, the azeotrope in the top stream is composed of 91% by weight of 4-methyl-5-n-butoxyoxazole and 9% by weight of tri-n-butylamine.

The tri-n-butylamine may be removed from the azeotrope in this case, for example, by a subsequent second rectification at a top pressure of 10 mbar.

The batchwise and semi-batchwise processing methods may be carried out in the presence or absence of solvents. In a preferred embodiment, the process is carried out without solvents.

However, it is also possible to add solvents or to use crude mixtures in the process according to the invention which, as well as the α-isocyanoalkanoate esters of the formula II and the assistants, already contain solvent.

In a further preferred embodiment, the process according to the invention is carried out in the presence of an inert solvent. Preferred inert solvents include nonpolar and polar aprotic solvents such as toluene, xylene or chlorobenzene, dichloromethane, dichloroethane, dichlorobenzene, ethylene carbonate, propylene carbonate, and in particular chlorobenzene.

This involves, in the batchwise or semi-batchwise processing method, first removing the low-boiling solvent and then the 5-alkoxy-substituted oxazole of the formula I by rectification.

In a particularly preferred embodiment of the process according to the invention, the processing method is continuous.

The continuous processing method involves continuously adding the α-isocyanoalkanoate esters of the formula II and the assistants either as a mixture or separately to a reactor, converting the α-isocyanoalkanoate esters of the formula II to the 5-alkoxy-substituted oxazoles of the formula I in the reactor and then continuously withdrawing the reaction products from the reactor, while, simultaneously with the conversion, continuously removing the 5-alkoxy-substituted oxazoles of the formula I from the reaction mixture.

There are many reactor designs which are useful for the particularly preferred continuous processing method. Preferred reactors should have the characteristic of facilitating a continuous conversion while simultaneously removing a reaction product.

Examples of useful reactors for the continuous processing method include stills having emplaced columns, extraction columns, bubble-cap tray columns, membrane reactors, Lord reactors or reaction columns.

As stated above, the term column, unless otherwise stated, refers to a column construction having a liquid phase.

Reaction columns are preferably columns whose internals have a hold-up, for example, columns having trays, beds, structured packings or random packings.

In a particularly preferred embodiment of the process according to the invention, the continuous processing method is carried out in a reaction column as reactor and, simultaneously with the conversion, the 5-alkoxy-substituted oxazoles of the formula I are continuously removed from the reaction mixture by rectification.

The reaction columns may be configured as desired by the construction and the internals. Particular preference is given to the use of a dividing wall column as the reaction column.

A reaction column which can be configured in highly varied ways has the characteristic of being a reactor which can simultaneously facilitate a conversion of reactants and the removal by rectification of the 5-alkoxy-substituted oxazoles of the formula I from the reaction mixture.

In this particularly preferred embodiment employing a reaction column for a continuous processing method, it is also advantageous to set the rectification parameters in such a way that A the α-isocyanoalkanoate esters of the formula II are converted to the 5-alkoxy-substituted oxazoles of the formula I on the internals and, if present, in the liquid phase of the reaction column, B the 5-alkoxy-substituted oxazoles of the formula I resulting from the conversion are continuously removed with the top stream or side stream of the reaction column and C the assistants and any high-boilers resulting from the conversion are removed continuously and independently of each other with the bottom stream or side stream of the reaction column.

Depending on the design of the reaction column and the reactants used, this is achieved by different settings of the rectification parameters. Examples of suitable rectification parameters include temperature, pressure, reflux ratio in the column, configuration of the column and its internals, heat transfer and residence time, in particular in the liquid phase, and energy introduction, each of which may be optimized through routine experiments by those skilled in the art in such a way that the characteristics A, B and C are achieved.

In feature C, the assistant may in particular also be removed from the high-boilers in a second side stream.

For the purposes of the present invention, a side stream is the continuous discharge of a substance via a side stream take off of the column.

For the continuous processing method of the process according to the invention, the pressure at the top of the column is also set in such a way that the temperature in the liquid phase and on the internals is at least 80° C., preferably from 100 to 200° C., more preferably from 120 to 170° C., most preferably from 130 to 170° C.

Typically, the top pressure of the column for the continuous processing method is set to from 5 to 800 mbar, in such a way that the bottom pressure resulting from the column type used and the tanks of any column internals used is typically from 5 mbar to atmospheric pressure.

The residence time in the reaction column for the continuous processing method is typically between 10 minutes and 7 hours, preferably from 30 minutes to 4 hours.

It is also possible in the continuous processing method that the 5-alkoxy-substituted oxazoles of the formula I form an azeotropic mixture with the assistants used so that the 5-alkoxy-substituted oxazoles of the formula I are removed via the top stream as an azeotropic mixture.

In this case, it is advantageous to set the top pressure and therefore also automatically the bottom pressure in the column in such a way that, depending on the 5-alkoxy-substituted oxazole of the formula I prepared and the assistant used, the fraction of assistant in the azeotrope in the top stream is as low as possible.

The assistant is removed from the top stream azeotrope in this case by a manner known per se, for example by a subsequent second rectification using a different pressure (two-pressure distillation).

The continuous processing method of the process according to the invention may be carried out in the presence or absence of solvents. In a preferred embodiment, the continuous processing method of the process according to the invention is carried out without solvents.

In a further preferred embodiment, the continuous processing method of the process according to the invention is carried out in the presence of an inert solvent. Preferred inert solvents include nonpolar and polar aprotic solvents such as toluene, xylene or chlorobenzene, dichloromethane, dichloroethane, dichlorobenzene, ethylene carbonate, propylene carbonate, and in particular chlorobenzene.

When a solvent is used, the solvent may be added continuously to the column, for example, in a mixture with the assistant and the α-isocyanoalkanoate esters of the formula II or each individual component may be added separately.

When an inert solvent is used in the continuous processing method of the process according to the invention, preference is given to setting the rectification parameters in such a way that A the α-isocyanoalkanoate esters of the formula II are converted to the 5-alkoxy-substituted oxazoles of the formula I on the internals and, if present, in the liquid phase of the reaction column, B1 when the solvent has a higher boiling point than the 5-alkoxy-substituted oxazoles of the formula I resulting from the conversion, the 5-alkoxy-substituted oxazoles of the formula I are continuously removed with the top stream and the solvent is continuously removed via the side stream or bottom stream of the reaction column, B2 when the solvent has a lower boiling point than the 5-alkoxy-substituted oxazoles of the formula I resulting from the conversion, the 5-alkoxy-substituted oxazoles of the formula I are continuously removed with a side stream and the solvent is continuously removed with the top stream of the reaction column and C the assistant and any high-boilers resulting from the conversion are removed continuously and independently of each other with the bottom stream or side stream of the reaction column.

The internals used in the reaction column may be of any design, for example, column trays, beds, random packings or structured packings.

Particularly advantageous column trays facilitate a long residence time of the liquid, and the residence time on the internals of the reaction column is preferably at least 30 min.

Examples of preferred column trays include valve trays, preferably bubble-cap trays, or related designs, for example, tunnel trays, Lord stages and other internals or Thormann trays.

Examples of preferred structured packings include structured packings of the Mellapack® (Sulzer), BY® (Sulzer), B1® (Montz) or A3® (Montz) types or packings having comparable designs.

The process according to the invention has the following advantages over the prior art:

The process according to the invention achieves selectivities of over 95% based on the α-isocyanoalkanoate esters of the formula II used.

The conversion is almost 100%, so that the yields of 5-alkoxy-substituted oxazoles of the formula I are over 95%, based on the α-isocyanoalkanoate esters of the formula II used.

The particularly preferred continuous processing method has the further advantage of a distinctly greater space-time yield than the prior art processes.

The process according to the invention provides a novel and advantageous contributory synthetic step in the process for preparing pyridoxine derivatives of the formula IX,

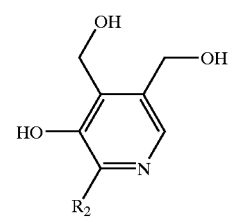

IX in particular for preparing pyridoxine (vitamin $B_6$; formula IX, $R_2$=methyl).

The invention accordingly also relates to a process for preparing pyridoxine derivatives of the formula IX which comprises converting amino acids of the formula III

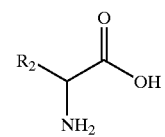

III to amino acid esters of the formula IV,

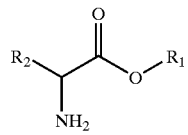

IV converting the latter into formamido esters of the formula V,

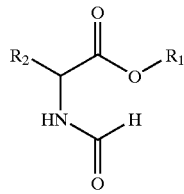

V converting the latter into α-isocyanoalkanoate esters of the formula II,

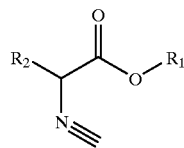

II converting the latter in the presence of assistants at temperatures above 80° C. to the 5-alkoxy-substituted oxazoles of the formula I

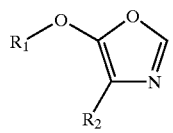

I and, simultaneously with the conversion, removing the 5-alkoxy-substituted oxazoles of the formula I from the reaction mixture, reacting the 5-alkoxy-substituted oxazoles of the formula I with protected diols of the formula VI,

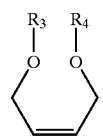

VI where $R_3$ and $R_4$ independently or $R_3$ and $R_4$ together are a protecting group of the hydroxyl function, to give the Diels-Alder adducts of the formula VII,

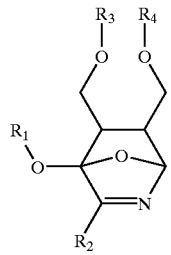

VII and converting the latter by acid treatment and detachment of the protecting group to the pyridoxine derivatives of the formula IX.

The overall process is, apart from the novel, advantageous contributory step according to the invention for the conversion of α-isocyanoalkanoate esters of the formula II to 5-alkoxy-substituted oxazoles of the formula I, disclosed by Ullmann's Encyclopedia of Industrial Chemistry 1996, Vol. A 27, pages 533 to 537.

The starting materials for the overall synthesis are inexpensive amino acids of the formula III, preferably alanine ($R_2$=methyl). These are converted in a manner known per se, for example by acid-catalyzed esterification with the alcohols $R_1$—OH, preferably n-butanol to amino esters of the formula IV. This esterification may also be achieved by other methods, for example, by activating the acid function and basecatalyzed esterification. Further methods are described in U.S. Pat. No. 3,227,721.

The amino acid esters of the formula IV are converted in a manner known per se, for example as described in U.S. Pat. No. 3,227,721, to the formamido esters of the formula V.

The formamido esters of the formula V are then converted in a manner known per se, as described above, to the α-isocyanoalkanoate esters of the formula II.

The α-isocyanoalkanoate esters of the formula II are converted, as described above, by the process according to the invention to the 5-alkoxy-substituted oxazoles of the formula I.

In the preferred overall process, this contributory step is carried out in the preferred embodiments, as described above.

The 5-alkoxy-substituted oxazoles of the formula I are then reacted with protected diols of the formula VI to give the Diels-Alder adducts of the formula VII.

This contributory step may be downstream of the process according to the invention, but, in the continuous processing method of the process according to the invention, may also be carried out by continuously adding the protected diols of the formula VI to the reactor of the process according to the invention simultaneously with the conversion of the α-isocyanoalkanoate esters of the formula II to the 5-alkoxy-substituted oxazoles of the formula I. The addition may be carried out either in a mixture with the α-isocyanoalkanoate esters of the formula II, the assistant and any solvent or as a separate component. In this case, the 5-alkoxy-substituted oxazole products are withdrawn directly in the form of their Diels-Alder adducts via the bottom discharge of the column.

The $R_3$ and $R_4$ radicals are each independently a protecting group, preferably an acid-labile protecting group, of the hydroxyl function.

In principle, any acid-labile protecting group may be used. Preferred acid-labile protective groups are the acid-labile protecting groups for hydroxyl groups known from the literature (T. W. Greene, Protective Groups in Organic Synthesis, John Wiley & Sons New York, 1981, pages 14–71; P. J. Kocienski, Protecting Groups, Georg Thieme Verlag Stuttgart, 1994, pages 21–94).

In a preferred embodiment, the $R_3$ and $R_4$ radicals together may also form an acid-labile protecting group of both hydroxyl functions. The two hydroxyl functions preferably form a cyclic acetal with ketones or aldehydes, for example, acetone or isobutyraldehyde.

Subsequent acid treatment of the Diels-Alder adducts of the formula VII with elimination of the alcohol $R_1$—OH results in aromatization to give the pyridoxine skeleton. The cleavage of the acid-labile protecting group(s) which is generally carried out aqueous acid treatment delivers the pyridoxine derivatives of the formula IX, in particular pyridoxine (vitamin B6, $R_2$=methyl).

The alcohol $R_1$—OH and the protecting groups $R_3$ and $R_4$ may be recovered and reused in the overall process.

The use of the novel advantageous contributory step according to the invention in the overall process leads to an increase in the overall yield.

The following examples illustrate the invention:

EXAMPLE 1
Continuous Preparation of 4-methyl-5-n-butoxyoxazole in a Dividing Wall Column A continuously operated dividing wall column (4.8 m×64 mm) packed with 3×3 mm of $V_2A$ Raschig rings and a dividing wall of height 2.4 m having 60 theoretical plates was charged with a mixture of 20.5% by weight of n-butyl α-isocyanopropionate ($R_1$=n-butyl, $R_2$=methyl) and 79.5% by weight of tri-n-butylamine.

At 500 mbar top pressure and a bottom temperature of 165° C., 4-methyl-5-n-butoxyoxazole was withdrawn overhead as an azeotrope with tri-n-butylamine (90:10% by weight) having a boiling point of 158° C. High-boilers and tributylamine were withdrawn at the base of the column. The conversion was 98.4%, the selectivity 99%. The yield of 4-methyl-5-n-butoxyoxazole was 95% based on the n-butyl α-isocyanopropionate used.

The azeotrope was then separated in the same column at a top pressure of 10 mbar. The top product obtained was an azeotrope having the composition 4-methyl-5-n-butoxyoxazole:tri-n-butylamine=70:30 and the side stream was pure 4-methyl-5-n-butoxyoxazole having a boiling point of 98° C. The distillation yield was 99% (40% of pure 4-methyl-5-n-butoxyoxazole and 60% of 4-methyl-5-n-butoxyoxazole as an azeotrope which was recycled into the first distillation). The pure 4-methyl-5-n-butoxyoxazole had a purity of 99.8%.

EXAMPLE 2
Continuous Preparation of 4-methyl-5-n-butoxyoxazole in a Dividing Wall Column Using a Solvent A continuously operated dividing wall column (4.8 m×64 mm) packed with 3×3 mm $V_2A$ Raschig rings and a dividing wall of height 2.4 m having 60 theoretical plates was charged with a mixture of 13.1% by weight of n-butyl α-isocyanopropionate ($R_1$=n-butyl, $R_2$=methyl), 32.2% by weight of monochlorobenzene and 50.1% by weight of tri-n-butylamine.

At 300 mbar top pressure and a bottom temperature of 169° C., monochlorobenzene having a boiling point of 90° C. was withdrawn overhead, and the side stream was an azeotrope of 4-methyl-5-n-butoxyoxazole with tri-n-butylamine (88:12% by weight) having a transition temperature of 151° C. High-boilers and tributylamine were withdrawn at the base of the column. The conversion was 99.5%, the selectivity 99%. The yield of 4-methyl-5-n-butoxyoxazole was 94%, based on the n-butyl α-isocyanopropionate used.

The azeotrope was separated according to Example 1.

EXAMPLE 3
Continuous Preparation of 4-methyl-5-n-butoxyoxazole in a Reaction Column Using a Solvent A column according to example 1 but without a dividing wall (see FIG. 1) was continuously charged via inlet (A) with a mixture of 20.6% by weight of chlorobenzene, 5.2% by weight of n-butyl α-isocyanopropionate ($R_1$=n-butyl, $R_2$=methyl) and 72.60% by weight of tris(2-ethylhexyl) amine.

At a top pressure of 300 mbar and a bottom temperature of 165° C., the solvent was withdrawn overhead (B). The 4-methyl-5-n-butoxyoxazole was obtained via side stream take off (C) in a yield of 99%. The amine was discharged via the bottom take off (E).

EXAMPLE 4
Continuous Preparation of 4-methyl-5-n-butoxyoxazole in a Reaction Column Example 3 was repeated, except that a mixture of 13.14% by weight of n-butyl α-isocyanopropionate and 86.86% by weight of tris(2-ethylhexyl)amine was continuously added via inlet (A).

At a top pressure of 400 mbar and a bottom temperature of 165° C., the 4-methyl-5-n-butoxyoxazole was withdrawn via the top take off (B) and the amine was discharged via the bottom take off (E). The yield of 4-methyl-5-n-butoxyoxazole was 98.8%.

EXAMPLE 5
Continuous Preparation of 4-methyl-5-isobutoxyoxazole in a Reaction Column Example 3 was repeated, except that a mixture of 22.7% by weight of isobutyl α-isocyanopropionate and 77.3% by weight of N,N-dibutylaniline was added continuously via the inlet (A).

At a top pressure of 300 mbar and a bottom temperature of 160° C., the 4-methyl-5-isobutoxyoxazole was withdrawn at a temperature of 150° C. via the top take off (B). The amine was obtained via the side stream D at 161° C. The yield of 4-methyl-5-isobutoxyoxazole was 91%.

EXAMPLE 6
Continuous Preparation of 4-methyl-5-n-butoxyoxazole in a Reaction Column Example 5 was repeated, except that a mixture of 11.8% by weight of n-butyl α-isocyanopropionate and 88.2% by weight of N,N-dibutylaniline were added continuously via the inlet (A). 4-Methyl-5-n-butoxyoxazole was obtained in a yield of 98.7% via the top take off B and the amine via the side stream take off D.

EXAMPLE 7
Continuous Preparation of 4-methyl-5-butyloxyoxazole (MOX) in a Reaction Column Using n-butanol as a Cyclizing Assistant A continuously operated dividing wall column (4.8 m×64 mm) filled with 3×3 mm $V_2A$ Raschig rings and a dividing wall of height 2.4 m having 60 theoretical plates was charged with a mixture of 30% by weight of n-butyl α-isocyanopropionate and 70% by weight of n-butanol via inlet (A).

At a top pressure of 300 mbar and a bottom temperature of 165° C., n-butanol was removed overhead. The column liquid phase was maintained at a constant level by using di-n-butyl phthalate as an intermediate boiler.

In the side stream, 4-methyl-5-butoxyoxazole (MOX) was obtained in 97% purity in a yield of 94%.

EXAMPLE 8

Continuous Preparation of 4-methyl-5-butyloxyoxazole (MOX) in a Reaction Column Using n-butyl Propionate as a Cyclizing Assistant The apparatus and experimental operation corresponded to example 7.

Example 7 is repeated, except that a mixture of 35% by weight of n-butyl α-isocyanopropionate and 65% by weight of n-butyl propionate were added continuously.

At a top pressure of 300 mbar and a bottom temperature of 165° C., n-butyl propionate was removed overhead. The column liquid phase was maintained at a constant level using di-n-butyl phthalate as an intermediate boiler.

In the side stream, 4-methyl-5-butyloxyoxazole (MOX) was obtained in 95% purity in a yield of 92%.

We claim:

1.) A process for preparing 5-alkoxy-substituted oxazoles of the formula I,

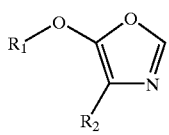

where
R$_1$ is an unsubstituted or substituted C$_1$–C$_6$-alkyl radical and
R$_2$ is hydrogen or an unsubstituted or substituted C$_1$–C$_6$-alkyl radical,
which comprises
converting α-isocyanoalkanoate esters of the formula II

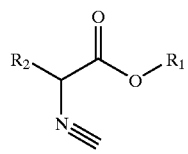

in the presence of assistants at temperatures above 80° C. into the 5-alkoxy-substituted oxazoles of the formula I and, simultaneously with the conversion, removing the 5-alkoxy-substituted oxazoles of the formula I from the reaction mixture, wherein said assistants are cyclizing assistants selected from the group consisting of tertiary amines, alcohols and substituted or unsubstituted C$_1$–C$_6$-alkanoates.

2. A process as claimed in claim 1, wherein the process is carried out batchwise.

3. A process as claimed in claim 2, wherein the process is carried out in a batchwise or semi-batchwise reactor equipped with an emplaced reaction column and, simultaneously with the conversion, removing the 5-alkoxy-substituted oxazoles of the formula I from the reaction mixture by rectification.

4. A process as claimed in claim 3, wherein the rectification parameters are set in such a way that D the α-isocyanoalkanoate esters of the formula II are converted to the 5-alkoxy-substituted oxazoles of the formula I in the reactor and/or on the internals of the emplaced reaction column and E the 5-alkoxy-substituted oxazoles of the formula I resulting from the conversion are removed via the emplaced reaction column.

5. A process as claimed in claim 2, wherein the conversion is carried out in the presence of an inert solvent.

6. A process as claimed in claim 3, wherein the reaction column used is a dividing wall column.

7. A process as claimed in claim 4, wherein the top pressure of the column is set to from 5 to 800 mbar and the resulting bottom pressure, which depends on the type of column used and, if used, the type of column internals, is from 10 mbar to atmospheric pressure.

8. A process as claimed in claim 1, wherein the process is carried out continuously.

9. A process as claimed in claim 8, wherein the process is carried out in a reaction column and, simultaneously with the conversion, the 5-alkoxy-substituted oxazoles of the formula I are removed from the reaction mixture by rectification.

10. A process as claimed in claim 9, wherein the rectification parameters are set in such a way that A the α-isocyanoalkanoate esters of the formula II are converted to the 5-alkoxy-substituted oxazoles of the formula I on the internals and, if present, in the liquid phase of the reaction column, B the 5-alkoxy-substituted oxazoles of the formula I resulting from the conversion are continuously removed with the top stream or side stream of the reaction column and C the assistant and any high-boilers resulting from the conversion are removed continuously and independently of each other with the bottom stream or side stream of the reaction column.

11. A process as claimed in claim 8, wherein the conversion is carried out in the presence of an inert solvent and the reaction parameters are set in such a way that A the α-isocyanoalkanoate esters of the formula II are converted to the 5-alkoxy-substituted oxazoles of the formula I on the internals and, if present, in the liquid phase of the reaction column, B1 when the solvent has a higher boiling point than the 5-alkoxy-substituted oxazoles of the formula I resulting from the conversion, the 5-alkoxy-substituted oxazoles of the formula I are continuously removed with the top stream and the solvent is continuously removed via the side stream or bottom stream of the reaction column, B2 when the solvent has a lower boiling point than the 5-alkoxy-substituted oxazoles of the formula I resulting from the conversion, the 5-alkoxy-substituted oxazoles of the formula I are continuously removed with a side stream and the solvent is continuously removed with the top stream of the reaction column and C the assistant and any high-boilers resulting from the conversion are removed continuously and independently of each other with the bottom stream or side stream of the reaction column.

12. A process as claimed in claim 9, wherein the reaction column used is a dividing wall column.

13. A process as claimed in claim 9, wherein, when the assistant forms an azeotrope with the 5-alkoxy-substituted oxazoles of the formula I, the top pressure of the column is set in such a way that the fraction of the assistant in the azeotrope in the top stream is as low as possible.

14. A process as claimed in claim 9, wherein the top pressure of the column is set to from 5 to 800 mbar and the resulting bottom pressure, which depends on the type of column used and, if used, the type of column internals, is from 10 mbar to atmospheric pressure.

15. A process for preparing pyridoxine derivatives of the formula IX

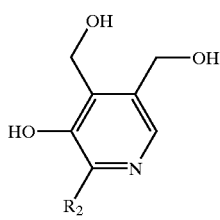

where
R$_2$ is hydrogen or an unsubstituted or substituted C$_1$–C$_6$-alkyl radical,
which comprises converting amino acids of the formula III

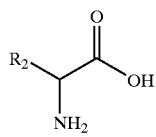

to amino esters of the formula IV,

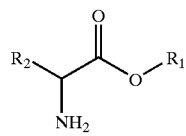

where
R$_1$ is an unsubstituted or substituted C$_1$–C$_6$-alkyl radical,
converting the latter into formamido esters of the formula V

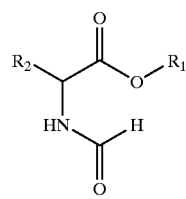

converting the latter into α-isocyanoalkanoate esters of the formula II,

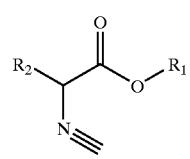

converting the latter in the presence of assistants at temperatures above 80° C. to the 5-alkoxy-substituted oxazoles of the formula I

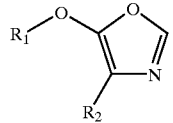

and, simultaneously with the conversion, removing the 5-alkoxy-substituted oxazoles of the formula I from the reaction mixture,
reacting the 5-alkoxy-substituted oxazoles of the formula I with protected diols of the formula VI,

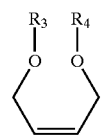

where
R$_3$ and R$_4$ independently or R$_3$ and R$_4$ together are a protecting group of the hydroxyl function,
to give the Diels-Alder adducts of the formula VII,

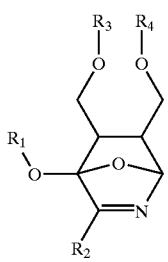

and converting the latter by acid treatment and detachment of the protecting group to the pyridoxine derivatives of the formula IX.

16. A process as claimed in claim 15, wherein the assistants used are cyclizing assistants selected from the group consisting of bases, alcohols and esters.

17. A process of claim 1 wherein the tertiary amines are triethylamine, triisopropylamine, tri-n-buytlamine, di-methylcyclohexylamine, tris(2-ethylhexy)amine, N-methylpyrrolidone, 5 N,N,N',N'-tetramethyl-1,3-propanediamine, N, N-diethylaniline or N,N-dibutylaniline.

18. The process of claim 17 wherein the tertiary amine is tri-n-butylamine.

19. The process of claim 16 wherein said bases are tertiary amines and said esters are substituted of unsubstituted C$_1$–C$_6$-alkyl C$_1$–C$_6$-alkanoates.

20. The process of claim 19 wherein said triethylamine, triisopropylamine, tri-n-butylamine, tertiary amines are di-methyl-cyclohexylamine, tris(2-ethylhexyl)amine, N-methylpyrrolidone, 5 N,N,N',N'-tetramethyl-1,3-propanediamine, N,N-diethylaniline or N,N-dibutylaniline.

21. The process of claim 1 wherein the cyclizing assistants are alcohols.

22. The process of claim 16 wherein the cyclizing assistants are alcohols.

* * * * *